United States Patent
Takabayashi et al.

(10) Patent No.: US 6,220,245 B1
(45) Date of Patent: Apr. 24, 2001

(54) VENTILATOR COMPRESSOR SYSTEM HAVING IMPROVED DEHUMIDIFICATION APPARATUS

(75) Inventors: Susumu Takabayashi, Oceanside; Raymond A. Ellestad, Vista, both of CA (US)

(73) Assignee: Mallinckrodt Inc., Hazelwood, MO (US)

( * ) Notice: Subject to any disclaimer, the term of this patent is extended or adjusted under 35 U.S.C. 154(b) by 0 days.

(21) Appl. No.: 09/243,724

(22) Filed: Feb. 3, 1999

(51) Int. Cl.[7] .................................................. A62B 19/00
(52) U.S. Cl. .............................. 128/205.12; 128/202.12; 128/202.13; 128/204.18
(58) Field of Search ........................ 128/203.13, 202.12, 128/205.12, 205.11, 204.23, 204.18, 204.16, 204.17, 204.28; 55/16; 95/52

(56) References Cited

U.S. PATENT DOCUMENTS

| | | |
|---|---|---|
| 4,727,871 | 3/1988 | Smargiassi et al. . |
| 4,867,151 | 9/1989 | Bird . |
| 5,082,471 * | 1/1992 | Athayde et al. ............................ 55/16 |
| 5,103,814 * | 4/1992 | Maher ................................ 128/204.18 |
| 5,237,987 | 8/1993 | Anderson et al. . |
| 5,240,472 * | 8/1993 | Sircar ....................................... 95/52 |
| 5,271,389 | 12/1993 | Isaza et al. . |
| 5,315,989 * | 5/1994 | Tobia ................................ 128/204.28 |
| 5,349,945 * | 9/1994 | McComb ............................ 128/203.17 |
| 5,362,207 * | 11/1994 | Martin et al. ............................ 417/243 |
| 5,383,449 | 1/1995 | Forare et al. . |
| 5,501,212 | 3/1996 | Psaros . |
| 5,505,768 | 4/1996 | Altadonna . |
| 5,632,805 | 5/1997 | Woodard . |
| 5,681,368 | 10/1997 | Rahimzadeh . |
| 5,850,833 * | 12/1998 | Kotliar .............................. 128/202.12 |
| 6,027,546 * | 2/2000 | Kusters et al. ............................ 95/52 |

OTHER PUBLICATIONS

Product Brochure re Stealth® .
Product Brochure re Parker Filtration –Finite®Compressed Air and Gas Dryers.

* cited by examiner

Primary Examiner—Glenn K. Dawson
Assistant Examiner—V. Srivastava
(74) Attorney, Agent, or Firm—Hovey, Williams, Timmons & Collins

(57) ABSTRACT

An improved compressor system (10) designed for use with a patient assist medical ventilator is provided which includes a compressor (12) and a pressurized gas delivery conduit (14); a hollow fiber membrane dryer (16) is interposed within the conduit (14) for final dehumidification of the pressurized gas and suppression of the dew point thereof In preferred forms, the membrane dryer output air may be recycled via a conduit (50) to the compressor (12) during phases of the system operation, so that such dried, pressurized air may be mixed with ambient air and fed to the compressor (12).

11 Claims, 1 Drawing Sheet

VENTILATOR COMPRESSOR SYSTEM HAVING IMPROVED DEHUMIDIFICATION APPARATUS

BACKGROUND OF THE INVENTION

1. Field of the Invention

The present invention is broadly concerned with an improved ventilator compressor system adapted for use with as a part of or in conjunction with a medical ventilator. More particularly, the invention is concerned with such compressor systems which include a hollow fiber membrane drying module for dehumidifying pressurized air from a compressor and significantly reducing the dew point pressure thereof; this insures that compressed air delivered to the ventilator is free of condensed water. Preferably, a recycle line is provided for delivery of pressurized, dehumidified air back to the compressor inlet during low demand operation of the system, to reduce the moisture level of incoming air to the compressor.

2. Description of the Prior Art

Many critically ill patients require breathing assistance by way of supplemental oxygen or through the use of a ventilator. A ventilator either forces pressurized gas into the lungs (a positive pressure ventilator) or expands the chest cavity of the patient to draw gas into the lungs (a negative pressure ventilator). Ventilators typically provide mixtures of pressurized air and oxygen to a patient according to a prescribed schedule, such as a specific pressure profile or a specific gas volume delivery profile over time. Moreover, many ventilators can be adjusted to either force breaths or respond only to a patient's attempts to breath and assist in such breathing, or operate in some more complex pattern.

In order to provide a source of pressurized air, ventilators may be coupled to hospital wall air which provides high quality, dehumidified and pressurized air. To this end, many hospital wall systems employ dryers in the pressurized air lines for dehumidification purposes, typically refrigerant or desiccant dryers. Membrane type dryers have also been used in this context. In addition, portable ventilators are commonly equipped with a portable compressor system either to meet the full demand of the ventilator or as a backup for ventilators using hospital wall air. A problem with such portable compressor systems is that they tend to provide high humidity air which can condense and cause damage to internal components of the ventilator and potentially loss of breath support to a patient. Previous methods for controlling humidity in such compressor systems has included the use of copper coils or heat exchangers for cooling and condensing of compressor output air. The cooling of such copper coil or heat exchanger occur within the confines of the compressor module itself, and is therefore warmer than ambient air outside the compressor module. Therefore, any outlet air that is exposed to ambient air can cool and cause condensation of the saturated air delivered to the ventilator. A typical solution is to compress the gas to above the required output pressure, pass it through a heat exchanger/condenser, and then regulate it down to a lower pressure. This expands the partially de-humidified air to try to bring the dew point below the ambient temperature. The problems introduced by this approach are decreased efficiency (to overpressurize the air), added heat in the compressor, decreased compressor life, and potential for inadequate dew point depression if the heat balance and pressure ratios are not adequate for all potential environments and air demand conditions.

SUMMARY OF THE INVENTION

The present invention overcomes the problems outlined above and provides an improved compressor system which is equipped with a membrane dryer so as to materially dehumidify the pressurized gas (usually air) delivered to a ventilator with a significant reduction in the dew point temperature of such gas. Broadly speaking, the compressor systems of the invention include a compressor with a gas delivery assembly including a delivery conduit coupled with the compressor outlet and adapted for connection with a ventilator; a membrane dryer is operably interposed in the delivery conduit downstream of the compressor outlet for removing moisture from the pressurized gas.

In preferred forms, the overall compressor systems of the invention are in the form of self-contained, portable units which include a heat exchanger and coalescing filter between the compressor and membrane dryer. The heat exchanger and filter initially dehumidify the pressurized air prior to entrance thereof into the membrane dryer.

In addition, the dehumidified output air from the dryer is directed to a valve which delivers the pressurized, dehumidified air to an accumulator and to the ventilator; alternately, when the accumulator is full and during low ventilator demand (e.g., during patient exhale), the dehumidified air from the dryer is recycled back to the compressor inlet. This reduces the overall moisture load imposed on the compressor system.

DETAILED DESCRIPTION OF THE PREFERRED EMBODIMENT

Figure 1:
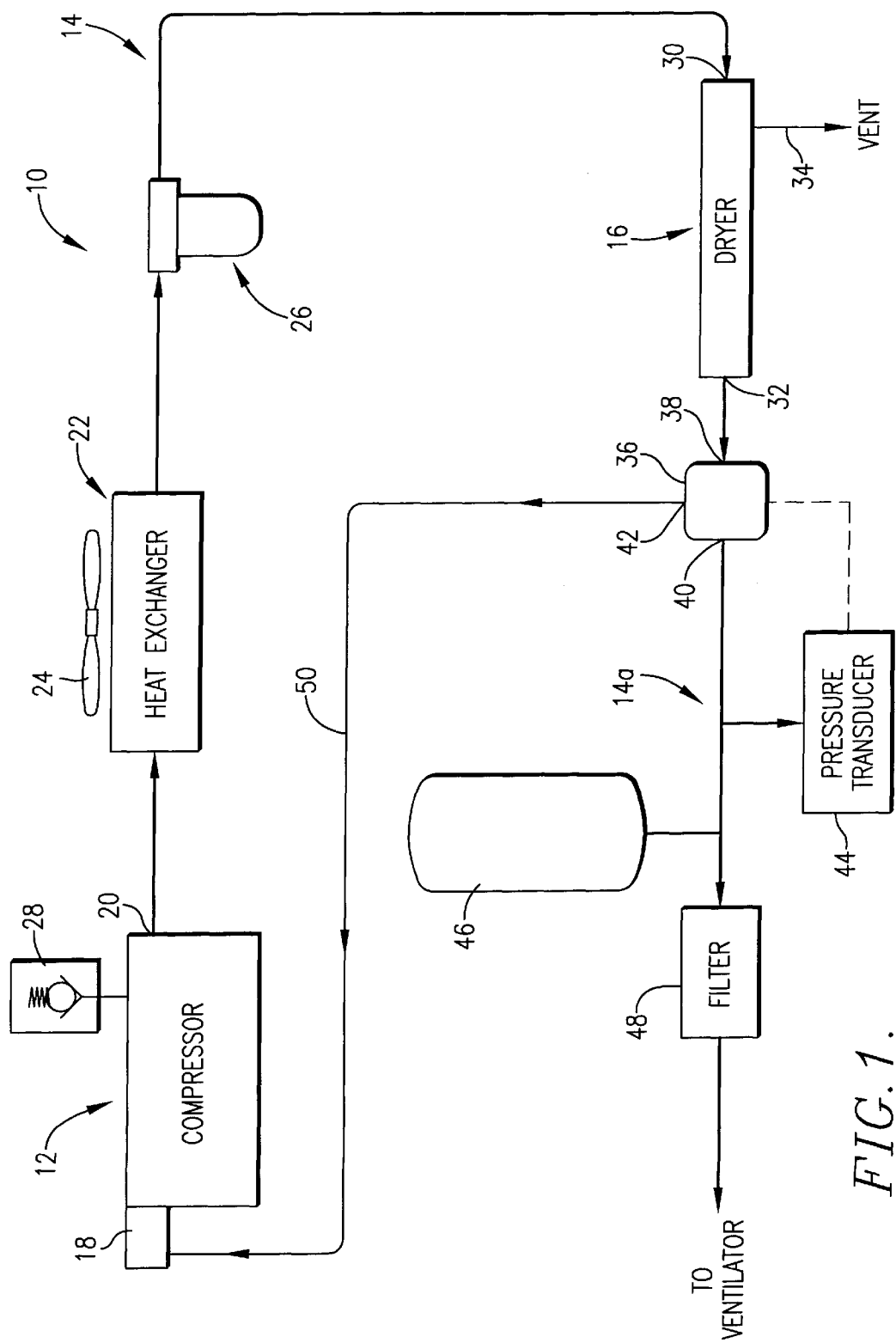
FIG. 1 is a schematic diagram illustrating the operative components of a preferred compressor system of the invention.

Turning now to the drawing, a compressor system 10 in accordance with the invention broadly includes a compressor 12 with a gas delivery conduit 14 leading to the other components of an overall patient ventilator, with a membrane dryer 16 interposed within conduit 14. Although not specifically illustrated in the drawing, it will be understood that the components of FIG. 1 are conventionally mounted on a wheeled or otherwise portable cart to form a self-contained compressor assembly which can be moved from room to room in a hospital or the like for connection to a ventilator.

In more detail, the compressor 12 is of a conventional two-piston design and has an inlet 18 equipped with a muffler/filter, and an outlet 20. The compressor 12 is operable for compressing ambient air (or a mixture of ambient and previously pressurized air) and producing a pressurized air outlet delivered through conduit 14. The compressor 12 also has an over-temperature thermostat to prevent overheating.

A heat exchanger 22 is interposed in conduit 14 downstream of compressor outlet 20 for cooling the pressurized air within the conduit 14. The exchanger 22 is of the finned tube design and has a pair of fans 24 for directing cooling air currents across the exchanger fins.

The output from exchanger 22 leads to a coalescing 0.3 micron filter 26 having an automatic water dump feature. The filter 26 operates so that the condensate created by heat exchanger 22 is automatically dumped out of the pneumatic circuit. Again, the filter 26 is of conventional design. A relief valve 28 is operably coupled compressor output port as shown. The relief valve prevents an overpressure condition within the conduit by venting to the atmosphere.

The membrane dryer 16 includes an input 30, an output 32 and a vent 34. Although a number of membrane filters can be used to good effect in the invention, the Stealth™ membrane dryers produced by Porous Media Corporation of St. Paul, Minn. are preferred. Such a dryer includes an outer housing containing hollow-fiber membranes. Compressed air flows through the dryer input 30, through the inside of the hollow fibers, and exits via outlet 32. The internal hollow fiber membranes preferentially allow water molecules to permeate and pass through the membrane walls, thereby dehydrating the compressed air stream. A portion of the dried, compressed air from the output 30 is introduced back into the shell side of the module, to flow over the fibers and remove the water molecules that have permeated through the membrane; such moisture-laden air is then vented via vent 34. This establishes a consistent dehydration and dew point suppression of the compressed inlet air.

The dried, compressed air from dryer 16 next passes through a directional valve 36 having an inlet port 38 and first and second outlet ports 40, 42. A downstream segment 14*a* of delivery conduit 14 is coupled to outlet port 40 as shown, and leads to the ventilator. A pressure transducer 44 is coupled with the segment 14*a* and valve 36, for controlling the operation of the latter in response to sensed pressure conditions. In addition, a large four-liter accumulator tank 46 is coupled to conduit segment 14*a* as shown, along with a final filter 48.

A makeup conduit 50 is coupled with port 42 of valve 36 and leads to the inlet 18 of compressor 12 so that, under certain system operations, dried, pressurized air is fed to the compressor 12.

The compressor system 10 is designed to operate in conjunction with a medical ventilator, such as the Sigma 840 ventilator commercialized by Nellcor Puritan Bennett, Inc. Thus, the segment 14*a* of delivery conduit 14 may be coupled with mixing apparatus for mixing the pressurized air output with oxygen for ultimate delivery to a patient. It will be appreciated, however, that the precise nature of the complete ventilator, and the hookup of system 10 thereto, are matters of design choice and are not pertinent to the present invention.

Considering the exemplary use of the system 10 in the context of a Sigma 840 ventilator, the system would preferably be in the form of a self-contained, portable unit designed to provide a source of pressurized room air to the ventilator sufficient to meet the ventilator's full flow requirements (i.e., continuous flow, peak flow, and maximum breath size). The compressor system 10 can be provided as a backup to a hospital wall air system, and as a complete source of air in cases where wall air is not available.

In use, the compressor system 10 is employed to maintain a supply of pressurized air within accumulator 46 at a design pressure typically between 22.5–25 psig. As ventilator demand reduces the pressure in the accumulator 46 to levels below 22.5 psig, as measured by transducer 44, the valve 36 is operated so as to couple inlet port 38 of the valve with outlet port 40, thereby recharging the accumulator.

When the accumulator is within its design pressure limits and ventilator demand is low, the valve 36 is diverted so that port 38 is coupled with outlet port 42; this diverts the pressurized, dehumidified air from dryer 32 back to the inlet 18 of compressor 12, thereby allowing mixing of such dehumidified air with ambient air. Such a recycling of the compressed, dehumidified air reduces the humidity of the air passing through the entire system and thus improves the dew point of the average output from dryer 16. Dryer efficiency is thus improved by a reduction in the moisture loading of the incoming air and by reducing the water collected on the outside of the hollow fiber membranes.

The operation of dryer 16 serves to suppress the dew point pressure of the compressed air passing through the conduit 14 by 3° C. or more, and more preferably from about 3–5° C. Generally, the input air to the dryer 16 is essentially saturated, and the dew point suppression effected by the filter 16 significantly enhances the quality of pressurized air delivered to the ventilator, so as to minimize the possibility of condensed water being delivered into the ventilator mechanism.

We claim:

1. A compressor system comprising:

a compressor having an input and a pressurized gas output;

a gas delivery assembly including a delivery conduit coupled with said compressor outlet, said assembly having a membrane dryer operably interposed in said delivery conduit for removing moisture from the pressurized gas passing through the delivery conduit; and a valve interposed in said delivery conduit downstream of said membrane dryer, said valve presenting an inlet port and first and second separately selectable outlet ports, said inlet port and said first outlet port being coupled with said delivery conduit, said second outlet port being coupled with a makeup conduit leading to and coupled with said compressor inlet, said valve operable for selectively directing dried gas to said makeup conduit so that such dried gas is passed into said compressor input.

2. The system of claim 1, including a heat exchanger interposed in said delivery conduit between said compressor unit and said membrane dryer for cooling of the pressurized gas within said delivery conduit.

3. The system of claim 2, including a water filter interposed in said delivery conduit between said heat exchanger and said membrane dryer.

4. The system of claim 1, including a pressure transducer operably coupled with said delivery conduit and said valve for controlling the operation of the valve in response to pressure conditions within said delivery conduit.

5. The system of claim 1, including an accumulator tank operably coupled with said delivery conduit downstream of said valve.

6. The combination comprising:

a medical ventilator; and a portable compressor system operably coupled with said ventilator, said compressor system comprising:

a compressor having an input and a pressurized gas output;

a gas delivery assembly including a delivery conduit coupled with said compressor outlet and adapted for connection with said ventilator, said assembly having a membrane dryer operably interposed in said delivery conduit for removing moisture from the pressurized gas passing through the delivery conduit; and a valve interposed in said delivery conduit downstream of said membrane dryer, said valve presenting an inlet port and first and second separately selectable outlet ports, said inlet port and said first outlet port being coupled with said conduit, said second outlet port being coupled with a makeup conduit leading to and coupled with said compressor inlet, said valve operable for selectively directing dried gas to said makeup conduit so that such dried gas is passed into said compressor input.

7. The combination of claim 1, including a heat exchanger interposed in said delivery conduit between said compressor unit and said membrane dryer for cooling of the pressurized gas within said delivery conduit.

8. The combination of claim 7, including a water filter interposed in said delivery conduit between said heat exchanger and said membrane dryer.

9. The combination of claim 6, including a pressure transducer operably coupled with said delivery conduit and said valve for controlling the operation of the valve in response to pressure conditions with said delivery conduit.

10. The combination of claim 6, including an accumulator tank operably coupled with said delivery conduit downstream of said valve.

11. The combination comprising:

a medical ventilator having a gas inlet;

a compressor having an input and a pressurized gas output; and a gas delivery assembly including a delivery conduit coupled with both said compressor outlet and with said ventilator inlet, said assembly having a membrane dryer operably interposed in said delivery conduit for removing moisture from the pressurized gas prior to passage thereof into said ventilator inlet, there being a valve interposed in said delivery conduit downstream of said dryer and having an inlet port and first and second separately selectable outlet ports, said inlet port and first outlet port coupled with said delivery conduit, said second outlet port coupled with a makeup conduit, said makeup conduit also coupled with said compressor input.

* * * * *